(12) United States Patent  
Swatton et al.

(10) Patent No.: US 10,368,967 B2  
(45) Date of Patent: Aug. 6, 2019

(54) ULTRASONIC DENTAL SCALER INSERT WITH ERGONOMIC GRIP DESIGN

(71) Applicant: DENTSPLY International Inc., York, PA (US)

(72) Inventors: Clive Swatton, Mount Joy, PA (US); Kenneth R. Guaragno, Spring Grove, PA (US); Jeremy Kile, Wrightsville, PA (US); Jared Witmer, Lewisberry, PA (US)

(73) Assignee: DENTSPLY SIRONA Inc., York, PA (US)

(*) Notice: Subject to any disclaimer, the term of this patent is extended or adjusted under 35 U.S.C. 154(b) by 63 days.

(21) Appl. No.: 14/484,325

(22) Filed: Sep. 12, 2014

(65) Prior Publication Data

US 2015/0072304 A1    Mar. 12, 2015

Related U.S. Application Data

(60) Provisional application No. 61/876,853, filed on Sep. 12, 2013.

(51) Int. Cl.  
*A61C 1/00* (2006.01)  
*A61C 1/08* (2006.01)  
*A61C 3/03* (2006.01)  
*A61C 17/20* (2006.01)

(52) U.S. Cl.  
CPC ............ *A61C 17/20* (2013.01); *A61C 1/0061* (2013.01); *A61C 1/08* (2013.01); *A61C 3/03* (2013.01)

(58) Field of Classification Search  
CPC ....... A61C 17/16; A61C 17/20; A61C 1/0061; A61C 1/08; A61C 1/10; A61C 1/14; A61C 1/145; A61C 3/03  
USPC .......................................................... 433/86  
See application file for complete search history.

(56) References Cited

U.S. PATENT DOCUMENTS

| | | | | |
|---|---|---|---|---|
| 3,075,288 | A | * | 1/1963 | Balamuth ................. A61C 1/07 433/86 |
| 3,809,977 | A | * | 5/1974 | Balamuth ................. A61C 1/07 15/22.1 |
| 3,919,775 | A | * | 11/1975 | Malmin .................... A61C 3/00 433/32 |
| 3,924,335 | A | * | 12/1975 | Balamuth ................. A61C 1/07 310/317 |
| 4,169,984 | A | * | 10/1979 | Parisi ...................... A61C 17/20 310/323.18 |
| 4,315,742 | A | * | 2/1982 | Nash ....................... A61C 17/20 433/86 |
| 4,370,131 | A | * | 1/1983 | Banko .................... B23Q 1/0036 433/119 |
| 4,406,284 | A | * | 9/1983 | Banko ..................... A61C 17/20 310/26 |
| 4,961,698 | A | * | 10/1990 | Vlock ..................... A61C 17/20 433/119 |
| 5,395,240 | A | * | 3/1995 | Paschke ................. A61C 17/20 433/119 |
| 5,419,703 | A | * | 5/1995 | Warrin ................... A61C 1/0084 433/216 |

(Continued)

*Primary Examiner* — Christopher A Flory  
(74) *Attorney, Agent, or Firm* — Dentsply Sirona Inc.

(57) ABSTRACT

A dental insert (10) has a nozzle (30) supporting a grip sleeve (80). Nozzle 30 may include several components (31, 32, 33) that are assembled without the need for a weld. A grip retaining ring 60 is positioned at a nodal location.

6 Claims, 6 Drawing Sheets

(56) References Cited

U.S. PATENT DOCUMENTS

| | | | | |
|---|---|---|---|---|
| 5,431,565 A * | 7/1995 | Euvrard | A61C 17/20 | 433/119 |
| 5,501,596 A * | 3/1996 | Bailey | A61C 17/20 | 433/119 |
| 5,725,370 A * | 3/1998 | Himeno | A61C 3/03 | 433/119 |
| 5,749,727 A * | 5/1998 | Dao | A61C 3/03 | 433/119 |
| 5,762,495 A * | 6/1998 | Pinel | A61C 1/052 | 433/126 |
| 5,775,901 A * | 7/1998 | Riso | A61C 17/20 | 433/119 |
| 5,853,290 A * | 12/1998 | Winston | A61C 17/20 | 433/119 |
| 5,915,965 A * | 6/1999 | Ohlsson | A61C 1/148 | 433/118 |
| 5,927,977 A * | 7/1999 | Sale | A61C 1/0061 | 433/119 |
| 5,975,896 A * | 11/1999 | Rainey | A61C 1/07 | 433/82 |
| 6,164,968 A * | 12/2000 | Feine | A61C 17/20 | 433/119 |
| 6,494,714 B1 * | 12/2002 | Copeland | A61C 3/03 | 433/119 |
| 6,716,028 B2 * | 4/2004 | Rahman | A61C 17/20 | 433/119 |
| 7,011,520 B2 * | 3/2006 | Rahman | A61C 17/20 | 433/86 |
| 7,140,878 B2 * | 11/2006 | Hickok | A61C 3/03 | 433/81 |
| 7,150,629 B2 * | 12/2006 | Feine | A61C 17/20 | 433/119 |
| 7,959,438 B2 * | 6/2011 | Feine | A61C 17/20 | 310/17 |
| 8,435,034 B2 * | 5/2013 | Gersh | A61C 17/20 | 433/119 |
| 8,585,404 B2 * | 11/2013 | Feine | A61C 17/20 | 433/119 |
| 2003/0124485 A1 * | 7/2003 | Teraushi | A61O 5/026 | 433/141 |
| 2004/0126736 A1 * | 7/2004 | Atkin | A61C 17/20 | 433/119 |
| 2004/0185412 A1 * | 9/2004 | Feine | A61C 17/20 | 433/29 |
| 2004/0259054 A1 * | 12/2004 | Mayer | A61C 17/20 | 433/119 |
| 2005/0008985 A1 * | 1/2005 | Nakanishi | A61C 1/18 | 433/86 |
| 2005/0032017 A1 * | 2/2005 | Levy | A61C 1/07 | 433/29 |
| 2005/0095556 A1 * | 5/2005 | Pollock | A61C 17/20 | 433/119 |
| 2006/0068361 A1 * | 3/2006 | Bergler | A61C 17/20 | 433/86 |
| 2006/0121413 A1 * | 6/2006 | Turner | A61C 1/05 | 433/114 |
| 2006/0234185 A1 * | 10/2006 | Ziemba | A61C 1/088 | 433/119 |
| 2007/0148618 A1 * | 6/2007 | Feine | A61C 17/20 | 433/119 |
| 2007/0190485 A1 * | 8/2007 | Hayman | A61C 1/07 | 433/118 |
| 2007/0190486 A1 * | 8/2007 | Khaimov | A61C 1/088 | 433/119 |
| 2008/0057469 A1 * | 3/2008 | Hayman | A61C 1/07 | 433/118 |
| 2008/0057470 A1 * | 3/2008 | Levy | A61C 1/00 | 433/118 |
| 2008/0096157 A1 * | 4/2008 | Ziemba | A61C 1/088 | 433/29 |
| 2008/0209650 A1 * | 9/2008 | Brewer | A46B 15/0002 | 15/22.1 |
| 2008/0318184 A1 * | 12/2008 | Zargari | A61C 1/07 | 433/119 |
| 2009/0017414 A1 * | 1/2009 | Andersson | A61C 1/088 | 433/29 |
| 2009/0081605 A1 * | 3/2009 | Hay | A61C 3/03 | 433/29 |
| 2009/0111070 A1 * | 4/2009 | Pollock | A61C 17/20 | 433/119 |
| 2009/0162810 A1 * | 6/2009 | Werner | A61C 17/20 | 433/119 |
| 2009/0202961 A1 * | 8/2009 | Fani | A61C 1/088 | 433/119 |
| 2009/0208899 A1 * | 8/2009 | Pond | A61C 5/02 | 433/81 |
| 2010/0261135 A1 * | 10/2010 | Feine | A61C 19/063 | 433/86 |
| 2011/0033823 A1 * | 2/2011 | Gersh | A61C 17/20 | 433/119 |
| 2011/0159454 A1 * | 6/2011 | Ziemba | A61C 1/088 | 433/29 |
| 2011/0229846 A1 * | 9/2011 | Chen | A61C 8/0089 | 433/86 |
| 2012/0028209 A1 * | 2/2012 | Werner | A61C 1/088 | 433/29 |
| 2012/0275098 A1 * | 11/2012 | Feine | A61C 1/0015 | 361/679.01 |
| 2012/0308956 A1 * | 12/2012 | DeVengencie | A61C 17/20 | 433/86 |
| 2013/0171582 A1 * | 7/2013 | Nishikibe | A61C 3/03 | 433/86 |
| 2013/0209955 A1 * | 8/2013 | Moran | A61C 3/03 | 433/86 |
| 2013/0337404 A1 * | 12/2013 | Feine | A61C 3/025 | 433/86 |
| 2014/0212831 A1 * | 7/2014 | Wagner | A61C 5/02 | 433/29 |
| 2014/0349248 A1 * | 11/2014 | Pond | A61C 1/0084 | 433/86 |
| 2014/0356808 A1 * | 12/2014 | Pond | A61C 3/03 | 433/86 |
| 2015/0111169 A1 * | 4/2015 | Yamamoto | A61C 17/20 | 433/86 |
| 2015/0333535 A1 * | 11/2015 | Feine | A61C 17/20 | 307/104 |
| 2016/0113733 A1 * | 4/2016 | Pond | A61C 5/02 | 433/86 |

* cited by examiner

ULTRASONIC DENTAL SCALER INSERT WITH ERGONOMIC GRIP DESIGN

TECHNICAL FIELD

The present invention is directed toward an ultrasonic dental scaler insert. More particularly, the invention relates to improvements in the gripping portion of the insert.

BACKGROUND OF THE INVENTION

The present invention provides an improved grip for ultrasonic inserts used with for example, magnetostrictive ultrasonic scaling devices. When used with proprietary ultrasonic scaling devices such as CAVITRON® by DENTSPLY INTERNATIONAL of York, Pa., the dental insert vibrates at an ultrasonic frequency to remove biofilm and calculus from the tooth and root surfaces while having cooling water flush away the removed deposits. The improved grip of the invention enhances softness, feel, and shape compared to the current insert grip designs in the industry. The grip is robust and resilient to the conditions of extreme temperature and pressure typical to autoclave environments, and to washer/disinfectant chemicals.

There is a trend in dentistry towards more comfortable, ergonomic equipment and instruments. A wider grip helps lessen hand fatigue to help maintain tactile sensitivity, as well as decrease the incidence of carpal tunnel syndrome.

Many useful dental instruments employ substantial vibratory motion at a tool tip of the instrument for cleaning, scaling and like operations. The tool tips are often designed to produce flexural and longitudinal vibrations with flexural motions of from about 0.02 to 0.2 mm. The tip is typically attached to an electro-mechanical part or section that can be induced to vibrate at high frequency. The instrument is driven for example, by an electronic generator at relatively high frequencies, typically on the order of above 20 kHz, to obtain adequate motion and to minimize objectionable noise since the human hearing threshold is about 18 kHz. The energy generator and related electro-mechanical section may be any one of several types such as electro-dynamic, piezo electric, or magnetostrictive. Design of the tip and its related electro-mechanical components involves combining a number of parameters to produce mechanical resonances (harmonic vibrations) at the driving frequency to produce amplified mechanical motion, particularly at the distal tip end.

In many operations employing a vibrating tip tool, it is useful and often necessary to have a source of water or other fluid impinging upon the workpiece surfaces and/or tool surfaces in order to cool them or remove debris generated by the work. For example, in dental applications, when an ultrasonically vibrated tip contacts a tooth surface, as required for performing a cleaning operation, the moving tip against the tooth surface produces heat. The patient may experience a pain sensation which can be severe if the operator applies even mild pressure against the tooth while cleaning. Water or some other fluid is usually supplied to the tooth surface in order to remove the heat and minimize pain and possible heat damage to the tooth. In addition, a number of the electro-mechanical devices utilized in providing a vibrating tip generate heat internally during operation.

An example of an ultrasonic dental tool, wherein a handpiece containing a coil applies an electro-magnetic field to a magnetostrictive insert body to which a tool tip is fixed is described by Perdreaux in U.S. Pat. No. Re. 30,536 which is hereby incorporated by reference for the general background of such devices. In the Perdreaux design, heat caused by electrical and mechanical friction losses within the tool during vibration are dissipated by means of a cooling fluid that flows axially with respect to the tool insert, over the active magnetostrictive element or stack, emerging from an annular space between the insert and the handpiece and being directed toward the working end of the tool. The arrangement is such that heat generated by the insert body warms the fluid which is then directed, as a convenient source of irrigating, flushing and/or cooling fluid, onto the active tip or workpiece area. The warm fluid minimizes reactions by patients who have sensitivity to cold temperatures.

In a number of dental operations, the vibrating tip is guided over and about tooth surfaces by the operator. The tip should be capable of penetrating between teeth and under or below the gingiva or gum line. Generally, the tip should be small in cross-section, ideally having a pointed tip with a tapered cross-section extending about 2.5 to 5 mm back from the distal tip end to allow adequate access between teeth and gingiva.

In addition, such tips are often curved or shaped to conform to or be compatible with tooth surfaces. Useful tips will curve sufficiently to permit spanning the tooth frontal surface when entrance to abutting surfaces is needed or when access to subgingival zones about the oral cavity are required.

It is often the case that an ultrasonically driven tool is configured so as to be connected to a part of the ultrasonic inducing element, such that the assembly can be inserted into a holder or handpiece or the like to complete the driving element. This is especially useful in the dental, medical or other fields where it may be necessary to clean and or sterilize the tool tip assembly apart from the remaining portions of the overall device. As an example, the FSI SLIMLINE series of ultrasonic inserts available from DENTSPLY INTERNATIONAL of York, Pa. have a tool connected to a magnetostrictive stack to form the insert. The insert is then inserted into a handpiece that provides the electrical connections to the insert to operate the thus assembled scaler device. After use, the insert can be removed from the handpiece and sterilized apart from the remaining portions of the device.

Inserts, such as the above mentioned FSI SLIMLINE inserts used to scale teeth, often have a gripping portion that's affixed to the insert such that this portion can be gripped by a user during use. It will be appreciated that such gripping portions should be configured so as to be ergonomically beneficial for the user. In the past such gripping portions have been made of various shapes and of various materials (such as Santoprene) to promote such comfort. These designs and materials of construction must be chosen to withstand the repeated sterilization procedures which often include the use of high heat exposure.

According to the present invention, the grip shape provides a finger rest preventing index or middle finger, depending on fulcrum, from slipping off insert. As a result the clinician can maintain a light grip and focus more on tip to tooth adaptation to improve both patient comfort and overall ergonomics. A one-piece grip is designed to enable easier cleaning. Grip texture is specially designed to lesson chance of slipping. Larger grip diameter is designed to lesson muscle load and pinch force. Grip texture is specially designed to increase friction with fingers, thereby requiring less pinching force.

Many current ultrasonic scaler inserts in the industry rely on a two part assembly that utilizes an ultrasonic weld to produce both a hermetic seal and a primary means of attachment in order to secure the plastic mold hand grip to the insert connecting body. The plastic molded parts must maintain a fluid tight seal and create an internal gland for a distal o-ring to seal between the connecting body and plastic molded halves of the grip. Users expect the dental insert to wear out, however prior to tips of the dental insert wearing beyond their usefulness, a water leak may develop which can make it difficult to maintain a proper grip (i.e. wet fingers) and irritate the patient by dripping water onto their face. The present Invention utilizes a construction that features a one-piece grip portion and which has separate features to secure the assembly and produce a hermetic seal.

As stated, current methods of assembling a grip onto an ultrasonic dental insert often include welding two substantially mirror image halves together using ultrasonic energy or the like. The ultrasonic welding operation uses friction to heat and melt the opposing plastic halves to form a joint. During the welding operation flash is squeezed out of the weld joint and requires removal. Removal includes a tedious manual step that has been eliminated in the invention disclosed herein. Beyond creating a cosmetic issue, the excess flash that is squeezed to the inside of the grip can allow flash particles to clog the fluid path.

It is evident from the state of the art that a new ultrasonic insert for use in vibratory activated tools would be desirable that includes an ergonomic gripping portion made without the previous disadvantageous welding procedures.

SUMMARY OF THE INVENTION

An insert for a dental, ultrasonic scaler assembly has a working tool having a fluid passage therein; a magnetostrictive stack; a connector body operatively connecting said tool to said magnetostrictive stack; a nozzle assembly having a connector body-receiving bore therein; and, a grip portion covering at least a portion of said nozzle assembly. The connector body has a passageway therein which is in fluid communication with a tool fluid passage. The said grip portion being of uni-body construction (that is, generally of one piece or substantially one-piece of formed material) having an end proximal and an and distal to said tool. The proximal end of said grip portion being provided with a tool receiving aperture and said distal end being provided with a nozzle assembly receiving aperture.

In one embodiment of the invention, the insert assembly is provided with a grip retaining ring positioned at a nodal location, and preferably is positioned on the connecting body. By "nodal location" it is meant a location where the standing wave imparted in the assembly during use assembly has no or substantially no or substantially reduced amplitude.

DETAILED DESCRIPTION OF THE EXEMPLARY EMBODIMENTS

Figure 9:
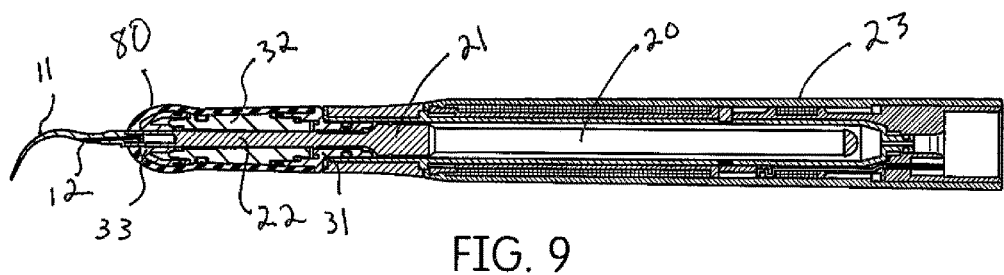
FIG. 9 is a sectional view of the insert of FIG. 1 shown inserted into a dental handpiece.

A dental insert embodying the concepts of the present invention is generally designated by the number 10 on the attached drawings. Insert 10 provides a working tool 11 of conventional design, preferably including a water conduit 12 therein for the passage of cooling water for use during scaling procedures, as is known to be advantageous in the art. Tool 11 is vibrated by conventional means such as by being connected to a magnetostrictive stack 20 through connecting body 21. Connecting body 21 preferably has an internal fluid passageway 22 in fluid communication with tool 11 and tool fluid conduit 12, again in a substantially conventional manner. Insert 10 may be inserted into a handpiece 23 (FIG. 9) which provides appropriate connections to electrical power and pressurized fluid (not shown). Handpiece 23 is of conventional design and carries the components necessary to induce a magnetic field in stack 20 as is known in the art.

Figure 1:
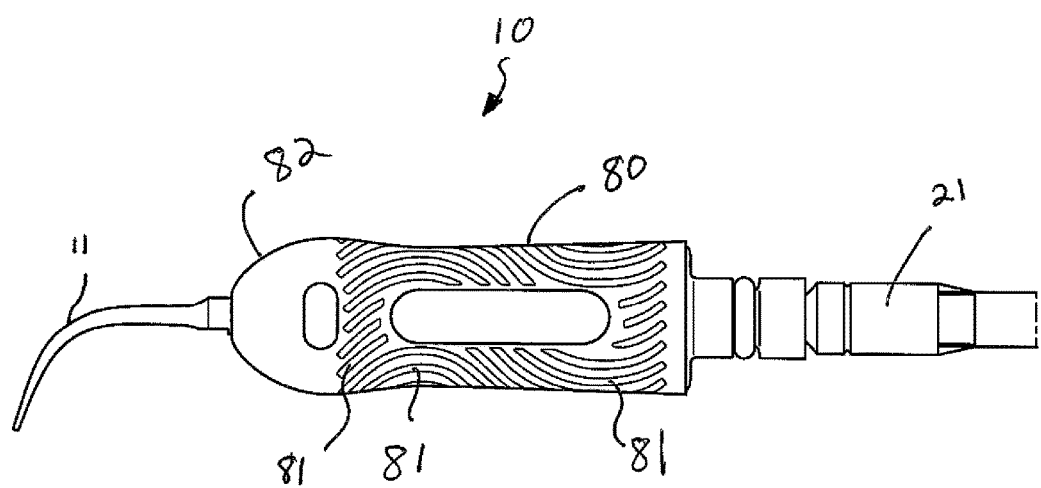
FIG. 1 is a close-up, side elevational portion of a portion of an ultrasonic scaler insert according to the present invention.
Figure 2:
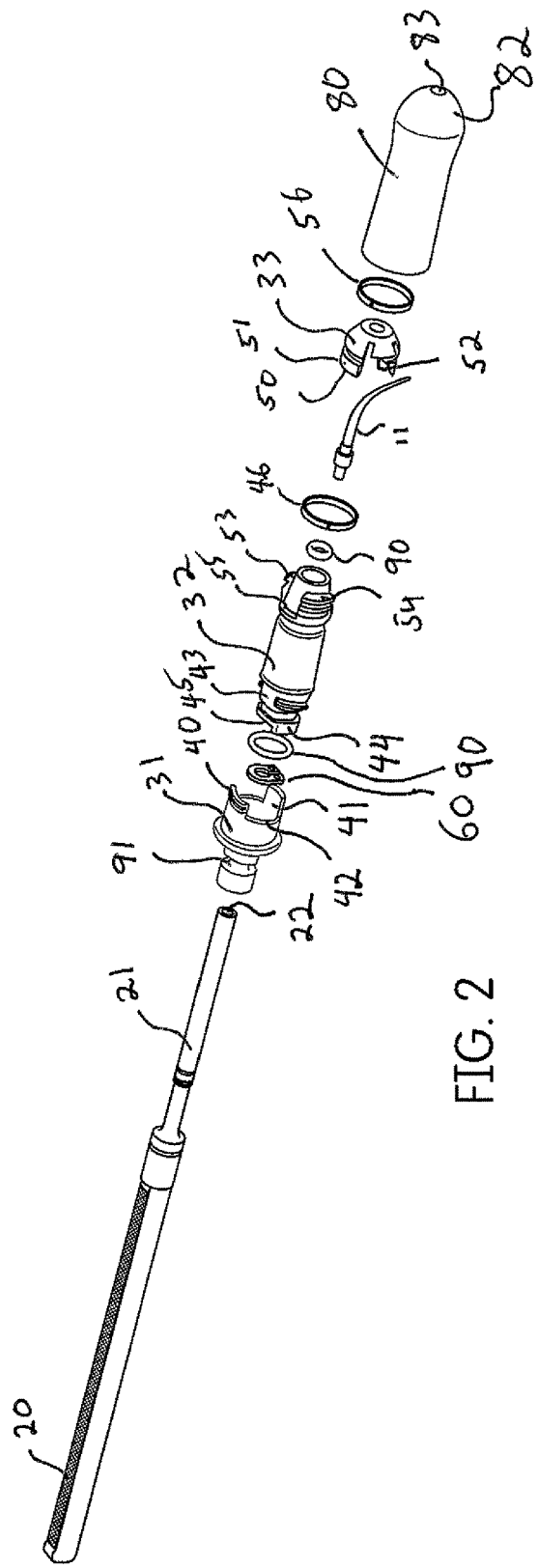
FIG. 2 is an exploded, perspective view of the entire ultrasonic scaler insert of FIG. 1.
Figure 3:
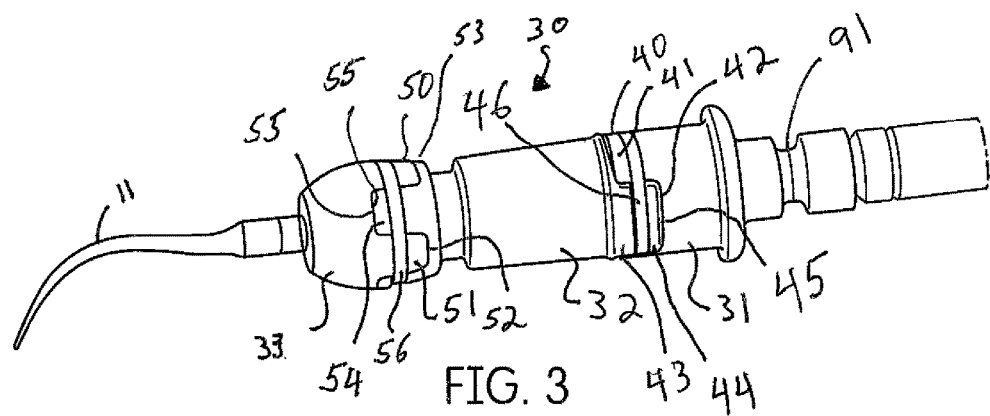
FIG. 3 is a side, perspective view of the insert of FIG. 1 without the grip portion.
Figure 4:
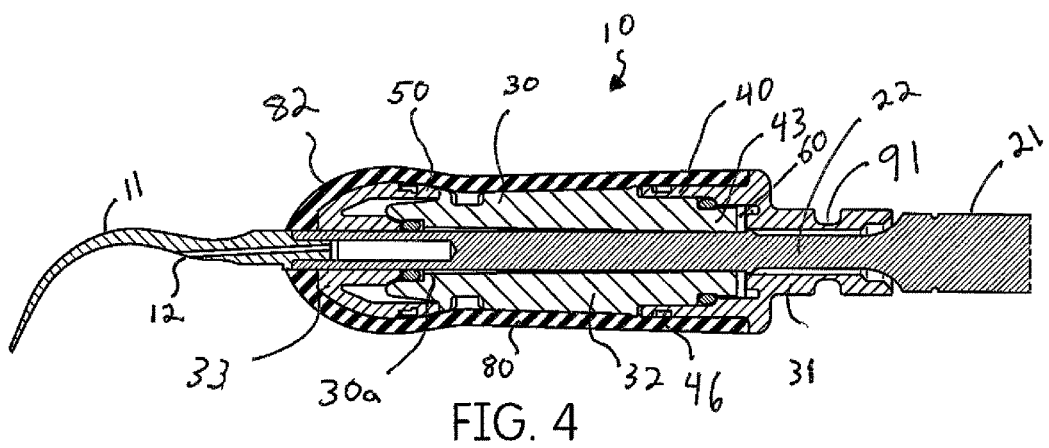
FIG. 4 is a cross section of the ultrasonic scaler insert of FIG. 1.

As shown in FIGS. 3 and 4, insert 10 includes a nozzle 30 configured to surround portions of connecting body 21 and tool 11 in use. Nozzle 30 has a bore 30a therethrough which is configured to receive at least a portion of connecting body 21. A continuous fluid path is thus formed by the fluid communication between the source (not shown), the internal fluid passageway 22 and the conduit 12. As stated above, in prior dental inserts, nozzles were provided that were fabricated from two substantially mirror image halves that were placed around the connecting body and welded in place, resulting in areas of potential weakness and leakage as well as unsightly or damaging flash. The present invention alleviates this problem by providing nozzle 30 which does not require such welding, although welding or even adhesive bonding could be employed if desired and still be within the scope of the invention.

Although nozzle 30 may be fabricated as a uni-body or one-piece construction, two-piece or any number of pieces, a preferred nozzle 30 according to the present invention includes three main components, namely a retainer or retaining nozzle 31, a middle nozzle part 32 and a nozzle nose 33. Retainer nozzle 31 is configured to connect to middle nozzle 32 which in turn connects to nozzle nose 33, in any suitable manner. By this construction, a substantially fluid-tight arrangement is achieved.

For example, retaining nozzle 31 may have an end 40 proximal to said middle nozzle 32 when assembled proximal end 40 of retaining nozzle 31 may be provided with at least one tab 41 and at least one notch 42. Middle nozzle 32 likewise has an end 43 proximal to retaining nozzle 31 when assembled. Proximal end 43 of said middle nozzle 32 similarly has at least one tab 44 and at least one notch 45 in a complementary shape to tab 41 and notch 42 of proximal end 40 of said retaining nozzle 31. When assembled for use, tab 41 of proximal end 40 of retaining nozzle 31 is receivable within notch 45 of proximal end 43 of middle nozzle 32, and tab 44 of middle nozzle 32 is receivable within notch 42 of proximal end 40 of retaining nozzle 31. The thus assembled connection is preferably secured in any conventional manner, and more preferably by use of a compression or hoopster ring 46. Similarly, nozzle nose 33 preferably has an end 50 proximal to middle nozzle 32 when assembled, wherein proximal end 50 of nozzle nose 33 has at least one tab 51 and at least one notch 52. Middle nozzle 32 has an end 53 proximal to nozzle nose 33 when assembled, wherein proximal end 53 of middle nozzle 32 has at least one tab 54 and at least one notch 55 in a complementary shape to tab 51 and notch 52 of proximal end 50 of nozzle nose 33. Tab 51 of proximal end 50 of nozzle nose 33 is receivable within notch 55 of proximal end 53 of middle nozzle 32. Tab 54 of middle nozzle 32 is receivable within notch 52 of proximal end 50 of nozzle nose 33. The thus assembled connection is preferably secured in any conventional manner, and more preferably by use of a compression or hoopster ring 56.

During assembly, nozzle 30 is positioned upon or receives within connector body 21. In order to retain nozzle 30 and prevent displacement, a grip ring 60 is preferably employed. An example of a useful grip ring 60 is depicted in the drawings as a split ring that can be positioned upon connecting body 21 and either resiliently compress upon connecting body 21 or be compressed thereupon during assembly. By being a ring shape, grip ring 60 can thus receive connecting body 21 therein. Grip ring 60 may thereby use friction to hold position and prevent rotation of nozzle 30 once installed on connecting body 21.

Figure 5:
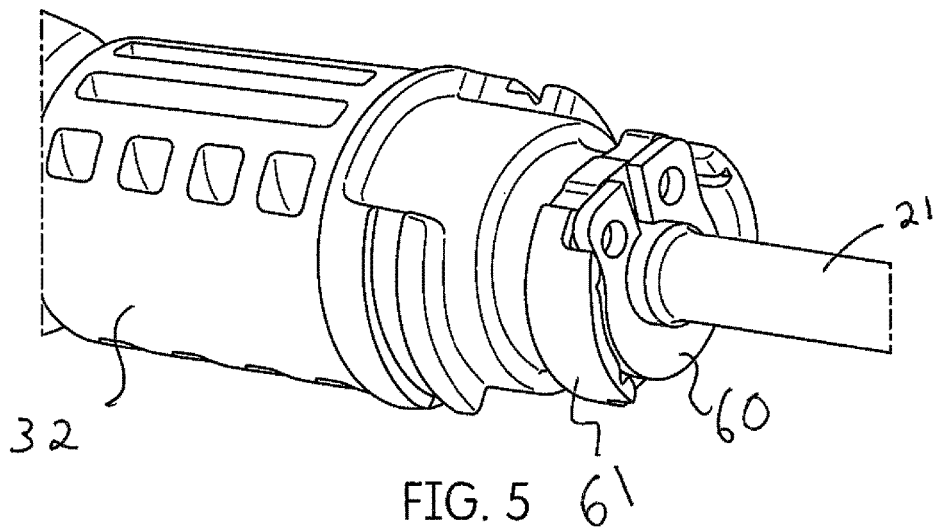
FIG. 5 is a close up, perspective view of one portion of the scaler of FIG. 1.
Figure 6:
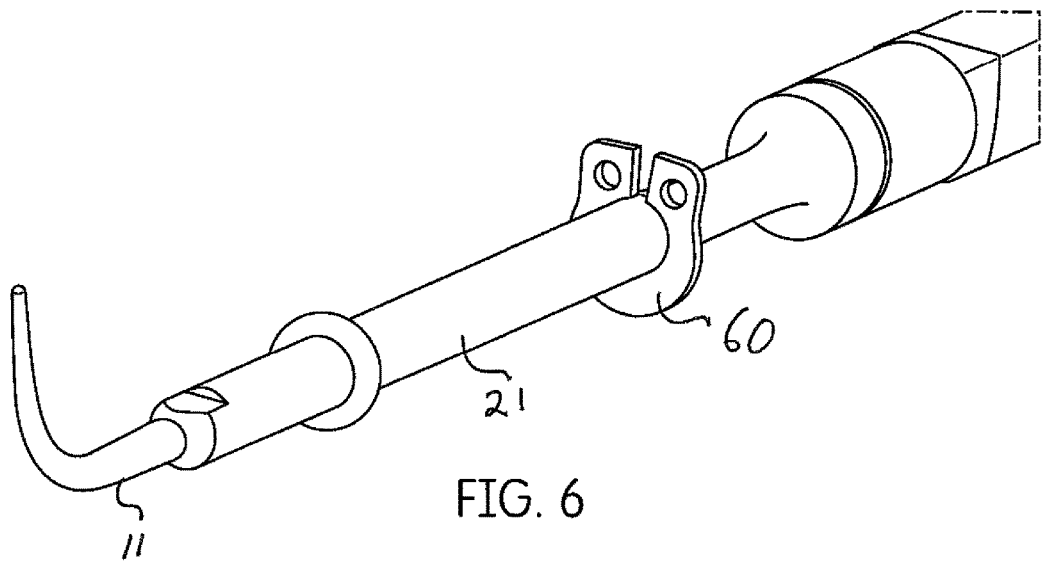
FIG. 6 is a perspective view of one portion of the scaler of FIG. 1.

Preferably and according to the invention, grip ring 60 secures ultrasonic dental insert 30 at a nodal location. A nodal location is a location along the ultrasonic insert that the vibrational standing wave has little to no amplitude. The nodal location includes a component that depends on friction between the metal (preferably stainless steel) connecting body 21 and the metal (again, preferably stainless steel) grip ring 60 to prevent axial movement and rotation. Grip ring 60 positions the other components of Insert 10 including nozzle 30, locating them such that the magnetostrictive stack 20 is accurately placed in the handpiece 23. Grip ring 60 clamps down on connecting body 21 such that it substantially is not moved without excesses forces (e.g. 10 lbs. axial and/or 3 lbs. torsional). Grip ring 60 may also provide asymmetrical features that help prevent other components of insert 10 to be engaged such that tool 11 will not rotate relative to a grip portion 60 to be described, or move axially. Grip ring 60 may be positioned at any desired location having the appropriate nodal function as above described. In the embodiment depicted in the drawings, grip ring 60 is positioned generally between middle nozzle 32 and retaining nozzle 31 when assembled. A cradle 61 may be provided (FIG. 5) to accommodate and otherwise support grip ring 60.

It will be appreciated that because grip ring 60 is fixed to connector body 21 and is prevented by friction or otherwise from moving apart from undue pressure or excess force as described, physical interaction between grip ring 60 and cradle 61 will likewise prevent or substantially prevent movement of nozzle 30. Although the invention has been characterized and shown on the drawings as employing a split-ring style grip ring 60, it will be appreciated that any such device or construction positioned at the nodal location as herein described, is within the scope of the invention, including for example, a full ring, a block or the like (not shown).

The nodal location placement of grip ring 60 may be determined by any conventional means. For example, an insert 10 according to the invention as described was fabricated, upon which a finite element analysis was performed using Solid Works Simulation software available from Solidworks Corp. of Waltham, Mass. The type of dynamic analysis used was a Modal Time History Analysis, where a time curve with a harmonic load at the resonant driving frequency was applied to the end of stack 20. This varying load represented the forcing function produced by the magnetostrictive stack 20, made of permanickel material, when subjected to the magnetic field.

Figure 7:
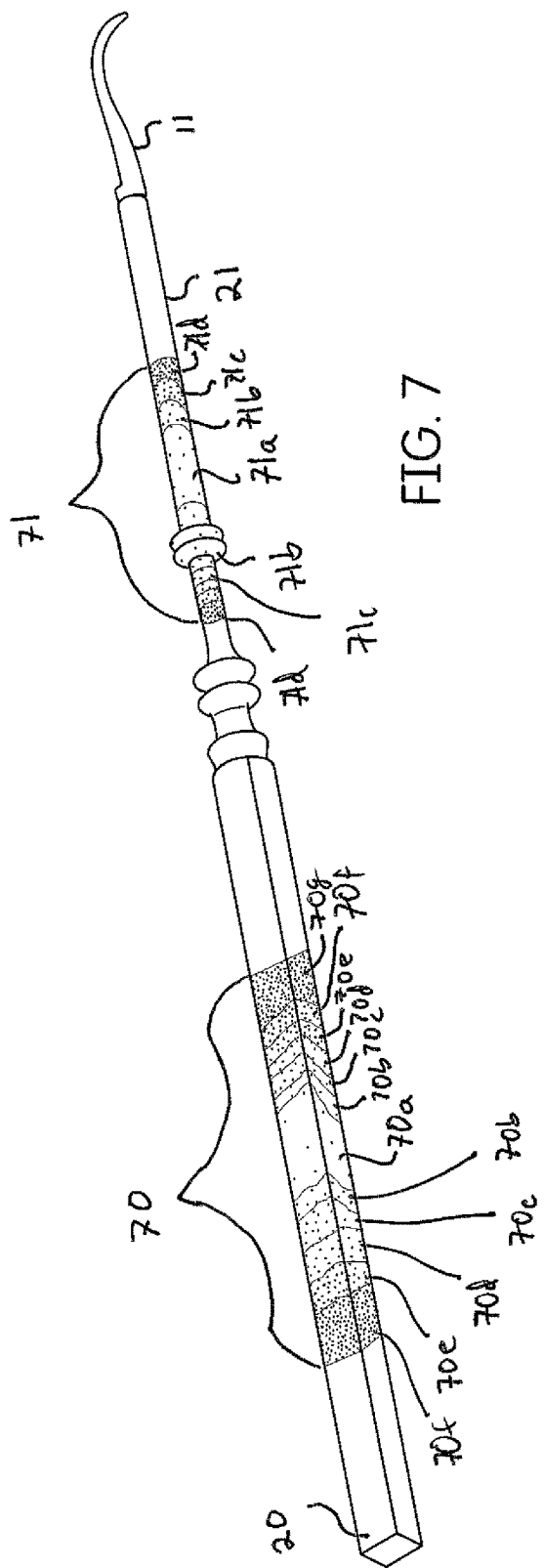
FIG. 7 is a side, perspective view of the scaler insert of FIG. 1 without the gripping portion, and showing an artistic representation of nodal zones of the insert when in actual use.
Figure 8:
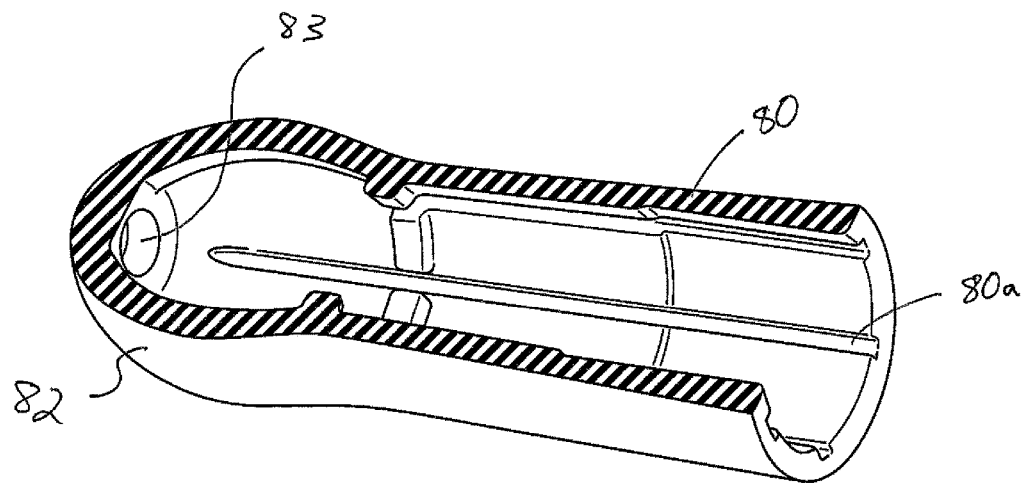
FIG. 8 is a close-up, perspective and cross sectional view of a portion of the grip portion of the insert in FIG. 1.

The equations of motion of this linear system exited by this time varying force is:

$$[M]\{\ddot{u}(t)\}+[C]\{\dot{u}(t)\}+[K]\{u(t)\}=\{f(t)\}$$

where:
  [M] is the symmetric inertia matrix
  [C] is the symmetric damping matrix
  [K] is the symmetric stiffness matrix
  $\{f(t)\}$ is the force vector
  $\{u\}$ is the displacement vector
  $\{\dot{u}\}$ is the velocity vector
  $\{\ddot{u}\}$ is the acceleration vector Using this approach, a graphic simulation of inventive insert 10 was made which indicated the nodal locations. FIG. 7 is a representation of the data thus obtained. Areas 70 and 71 represent such nodal locations. As shown, magnetostrictive stack 20 has a nodal location 70*a*, and areas of increasing vibration at areas 70*b*-70*g*. Similarly, connecting body 21 has a nodal location generally indicated by the number 71*a* and areas of increasing vibration at areas 71*b*-71*d*. Grip ring 60 would thereby be preferably indicated within area 71*a*. In this example, tool 11 was vibrated at a resonant frequency of about 29.6 kHz.

In a further aspect of the present invention, an outer grip sleeve 80 is provided. Preferably grip sleeve 80 is fabricated as a uni-body or one piece of a formed material such as a silicone rubber or the like. Silicone rubber has been found to withstand repeated sterilization and cleaning procedures better that the heretofore common use of santoprene or the like. In the embodiment of the invention as depicted in the drawings, nozzle 30 forms a skeleton that supports grip sleeve 80 and helps give it form, and may be provided with internal molded-in structures such as ridges 80*a* to further conform to and be supported by nozzle 30. Grip sleeve 80 may also be provided with external texture of contours 81 to facilitate gripping and manipulation by a user. Further, grip sleeve 80 preferably has a bulbous end 82 to further facilitate gripping and manipulation. The improved grip sleeve 80 of the invention is has enhanced softness, feel, and shape compared to the current insert grip designs. The grip is robust and resilient to the conditions of extreme temperature and pressure typical to autoclave environments, and to washer/disinfectant chemicals. There is a trend in dentistry towards more comfortable, ergonomic equipment and instruments. A wider grip as grip sleeve 80 provides helps lessen hand fatigue to help maintain tactile sensitivity, as well as decrease the incidence of carpal tunnel syndrome. Grip sleeve 80 is provided with an aperture 83 through which tool 11 can be inserted when assembled.

To hygienists concerned about ergonomics during ultrasonic scaling, the dental inserts with the grip sleeve 80 as disclosed herein, provides a dental insert 10 that helps prevent hand fatigue to maintain tactile sensitivity by providing a wide, comfortable grip. The unique grip shape described herein is designed to aid the hygienist in maintaining a proper relaxed grip while providing a convenient rest for their finger tip. The texture of the grip of the dental insert described herein is also a unique ripple pattern that is easy to clean, because it does not have deep crevices or pockets, can wick away fluids, and is subtle enough that it does not interfere with the clinician's tactile sensitivity.

Grip 80 bulbous end 82 as described provides a finger rest preventing the index or middle finger, depending on fulcrum, from slipping off the insert 10. As a result the clinician or user can maintain a light grip and focus more on tip to tooth adaptation to improve both patient comfort and overall ergonomics. Other advantages include a one-piece grip according to the invention enable easier cleaning, a grip texture 81 that is specially designed to lessen the chance of slipping, a larger grip diameter may lessen muscle load and pinch force, the grip texture is designed to increase friction with fingers, thereby requiring less pinching force.

Insert 10 may be provided with suitable O-rings 90 as is known in the art. As such, nozzle 30 or indeed any component of insert 10 may be suitable configured to receive and support such devices. For example, annular groove 91 may be provided in retaining nozzle 31 for this purpose. O-rings 90 made of a Viton material have been found to be advantageous. It will be appreciated that according to the invention, isolation of design elements as above described, separating mechanical assembly features and elements from seals, such that O-ring 90 seals assure a fluid tight assembly.

Thus, according to the invention, a dental insert is provided that is an improvement over known Inserts in the art. A grip ring is used to secure the grip at a nodal area. Compression rings such as hoopster rings are used to secure plastic molded parts. A bulbous or knuckle design that provides for the interlocking of two halves while allowing both sealing and engagement with connecting body nodal area grip ring features is provided. Isolation of design elements, separating mechanical assembly features and elements from seals, such that O-ring seals assure a fluid tight assembly and plastic parts have been provided to support various joining technologies, such as flame brazing, induction brazing, and laser welding to join tips to connecting bodies. The grip, hoopster ring and nose nozzle can be removed in order to facilitate the replacement of the associated O-ring. The grip shape, grip retention and mechanical interlock with nozzle assembly, and the interior ribs 80a of the grip 80 allow steam to sterilize the interior of the grip while allowing venting to prevent movement or inflation of the silicone grip during steam autoclave cycle. Thus, the present Invention is an advantageous improvement over known dental inserts.

Having thus described at least one illustrative embodiment of the invention, various alterations, modifications and improvements will readily occur to those skilled in the art. Such alterations, modifications and improvements are intended to be within the scope of the invention. Accordingly, the foregoing description is by way of example only and is not intended as limiting.

What is claimed is:

1. An insert for a dental, ultrasonic scaler assembly comprising:
   a working tool having a fluid passage therein; a magnetostrictive stack; a connecting body operatively connecting said tool to said magnetostrictive stack; a nozzle assembly having a connecting body-receiving bore therein; and, a grip portion covering at least a portion of said nozzle assembly
   said connecting body having a passageway therein which is in fluid communication with a tool fluid passage;
   said grip portion being of uni-body construction having an end proximal and an end distal to said tool; said proximal end of said grip portion being provided with a tool receiving aperture and said distal end being provided with a nozzle assembly receiving aperture, wherein said nozzle assembly comprises a retaining nozzle, a middle nozzle and a nozzle nose; and,
   a grip retaining ring positioned between said middle nozzle and said retaining nozzle, wherein the grip retaining ring positions the grip portion over the connecting body and prevents the grip portion from moving axially and radially;
   wherein the grip retaining ring locates the grip portion relative to the working tool, the magnetostrictive stack and connecting body; and
   wherein said retaining nozzle is configured to receive at least a portion of said connecting body, and to connect with said middle nozzle in a substantially fluid-tight manner.

2. The insert as in claim 1, wherein said retaining nozzle has an end proximal to said middle nozzle when assembled, said proximal end of said retaining nozzle having at least one tab and at least one notch; said middle nozzle having an end proximal to said retaining nozzle when assembled, said proximal end of said middle nozzle having at least one tab and at least one notch in a complementary shape to said at least one tab and at least one notch of said proximal end of said retaining nozzle; such that said at least one tab of said proximal end of said retaining nozzle is receivable within said at least one notch of said proximal end of said middle nozzle, and said at least one tab of said middle nozzle is receivable within said at least one notch of said proximal end of said retaining nozzle.

3. The insert as in claim 1, wherein said nozzle nose has an end proximal to said middle nozzle when assembled, said proximal end of said nozzle nose having at least one tab and at least one notch; said middle nozzle having an end proximal to said nozzle nose when assembled, said proximal end of said middle nozzle having at least one tab and at least one notch in a complementary shape to said at least one tab and at least one notch of said proximal end of said nozzle nose; such that said at least one tab of said proximal end of said nozzle nose is receivable within said at least one notch of said proximal end of said middle nozzle, and said at least one tab of said middle nozzle is receivable within said at least one notch of said proximal end of said nozzle nose.

4. The insert as in claim 1, wherein said grip portion has a bulbous end proximate to said tool such that the bulbous end further facilitates gripping and manipulation.

5. The insert as in claim 1, wherein said grip retaining ring is a split ring, such that said connecting body is receivable therethrough.

6. The insert as in claim 1, wherein said grip retaining ring is positioned at a nodal location on said connecting body.

* * * * *